(12) United States Patent
Perrad et al.

(10) Patent No.: US 6,706,003 B2
(45) Date of Patent: Mar. 16, 2004

(54) MUSCLE STRENGTH TESTING METHOD AND APPARATUS

(76) Inventors: Jacques Perrad, 408, rue Perreault, Chicoutimi, QBC (CA), G7J 3Y9; Julien Bouchard, 1355 Cartier, Ville St-Laurent, QBC (CA), H4L 2N7

( * ) Notice: Subject to any disclaimer, the term of this patent is extended or adjusted under 35 U.S.C. 154(b) by 59 days.

(21) Appl. No.: 09/780,465

(22) Filed: Feb. 12, 2001

(65) Prior Publication Data

US 2001/0029342 A1 Oct. 11, 2001

(30) Foreign Application Priority Data

Feb. 10, 2000 (GB) ............................................... 0002908

(51) Int. Cl.[7] .......................... A61B 5/103; A61B 5/117
(52) U.S. Cl. ..................... 600/587; 600/595; 73/379.01
(58) Field of Search ................................ 600/587, 595; 73/379.01, 379.02, 379.03, 379.08

(56) References Cited

U.S. PATENT DOCUMENTS

| | | | |
|---|---|---|---|
| 4,306,714 A | | 12/1981 | Loomis et al. |
| 4,501,148 A | * | 2/1985 | Nicholas et al. .......... 73/379.08 |
| 4,648,272 A | * | 3/1987 | Spector ....................... 177/245 |
| 4,702,108 A | | 10/1987 | Amundsen et al. |
| 4,732,038 A | | 3/1988 | DelGiorno et al. |
| 4,819,485 A | * | 4/1989 | DelGiorno et al. ...... 73/379.09 |
| 4,882,677 A | * | 11/1989 | Curran ........................ 600/587 |
| 4,944,309 A | | 7/1990 | Mechling |
| 5,029,592 A | * | 7/1991 | Schultz ....................... 600/587 |
| 5,038,795 A | | 8/1991 | Roush et al. |
| 5,317,916 A | | 6/1994 | Kovacevic |
| 5,471,885 A | | 12/1995 | Wagner |
| 5,597,373 A | | 1/1997 | Bond et al. |
| 5,911,693 A | * | 6/1999 | Prochazka et al. .......... 600/587 |
| 5,980,429 A | * | 11/1999 | Nashner ........................ 482/8 |
| 6,013,041 A | * | 1/2000 | Leathers ..................... 601/107 |
| 6,067,986 A | * | 5/2000 | Kluger et al. ............... 600/595 |
| 6,126,572 A | * | 10/2000 | Smith ............................ 482/4 |

* cited by examiner

*Primary Examiner*—Charles Marmor (57) ABSTRACT

An isometric muscle strength testing method and apparatus allow an intended examiner to qualitatively and subjectively assess the muscular contraction of a selected muscle, or group of muscles, of a patient through direct contact between the examiner's naked hand and the target segment of the patient that is anatomically coupled to the selected muscle. The method and apparatus allow a simultaneous quantitative and objective assessment of the strength of the muscular contraction through the use of a pressure sensor, without interfering on or modifying the conventional manual muscle test(s). The pressure sensor is positioned so that the force exerted by the selected muscle during contraction thereof is transmitted indirectly to the pressure sensor without direct contact between the pressure sensor and the patient target segment. A treatment table, or any other structure, can be positioned between the pressure sensor and either the patient or the examiner.

26 Claims, 8 Drawing Sheets

MUSCLE STRENGTH TESTING METHOD AND APPARATUS

FIELD OF THE INVENTION

The present invention relates to the field of gauging devices and is more particularly concerned with a muscle strength testing method and apparatus allowing simultaneous assessment of the muscular contraction of a selected muscle through direct contact between an examiner and a patient and assessment of the strength of the muscular contraction of the selected muscle through the use of a pressure sensor.

BACKGROUND OF THE INVENTION

Muscle strength can be defined as the ability of a muscle or a group of muscles to produce tension or exert force through the skeletal system. The generally accepted measurement criterion for the maximum tension which can be exerted by a muscle is the maximum amount of force a muscle can exert on a body part. In physiology, this is referred to as the maximum strength of the muscle and might be expressed, for example, in kilograms per square centimeter of muscular section. In day-to-day life with the patient, the strength is usually expressed in kilograms, Newtons, pounds or inch-pounds and Newton-meters.

There are a plurality of situations wherein it is desirable to monitor or test different muscle strength of an individual. This type of examination is commonly used in diagnostic, therapeutic and prevention activities. The tests are typically used to determine difference in strength between individuals and/or to determine strength deficits in a given individual. In such a case, deficits are detected by the comparison of contralateral limb segments or muscle groups. The tests are also typically used to monitor a patient's progress during a period of recovery or rehabilitation. Muscle testing is also used in the design of rehabilitation programs for injured patients or individuals wanting to undertake activities for which they are not properly conditioned.

Although the medical and therapeutic fields have evolved into high-tech sectors using state of the art technology, muscle strength testing which is part of most routine physical examination is still widely performed by a mere manual operation on behalf of an examiner. Muscle strength is typically tested by asking the patient or individual to move actively against the examiner's opposition (commonly called a make test) or to resist against the pressure of the examiner on a part of his/her body (commonly called a brake test) while the patient is asked to maintain a specific posture. The examiner is therefore able to subjectively judge the patient's maximum force, as conventionally called isometric manual muscle testing (MMT). Because of the sensitivity provided by the examiner, this method enables the examiner to assign a grade to indicate the weakness of the muscular contraction and to judge the qualitative aspect of the contraction such as slight shaking, saw-teeth type of effort or the like.

The strength is typically subjectively quantified and graded on a conventional zero to five scale. Although there are no international established standards, the grading scale varies between no muscular contraction detected (0) and active movement against full resistance without evident fatigue corresponding to normal muscle strength (5). Many clinicians make further distinction by using plus or minus signs towards the stronger and weaker end of the scale respectively. Thus, a (4+) grade indicates good but not full strength while a (5−) grade means a trace of weakness.

During the procedure, for purpose of comparison, the unaffected limb of the patient is typically similarly tested. From the hereinabove description, it is quite evident that the common manual method of muscle testing is opened to a large proportion of subjectivity.

Not only is the evaluation potentially unreliable when performed by a same individual but also this problem is compounded in situations wherein different individuals may use different techniques to perform the same testing.

Accordingly, several attempts to standardize manual testing procedures have been made and the prior art shows various devices adapted to measure muscle strength. For the most part, prior art devices suffer from a set of disadvantages including lack of ergonomical features, cumbersomeness, inability to test particular muscles or groups of muscles, complexity, lack of portability, expensiveness and so forth. One major drawback associated with some of the prior art devices is their inability to isolate specific muscles or muscle groups needing to be tested. Also, in the clinical context prior art testers have often proven to be difficult and time consuming to adjust to the specific ergonomical characteristics of the patient.

In order to test various body parts the devices always need to be quickly repositioned, thus failing to provide a practical solution, as opposed to quick displacements of the examiner to support and test these various body parts. As a result, despite the obvious disadvantages of the subjective test of muscle strength, manual testing without instrumentation continues to be the predominant method used in the clinical setting. One of the predominant factors is the so far unequaled ergonomical support provided by the examiner's hands since prior art devices, especially the handheld dynamometers (HHD), are often uncomfortable to the patient and unstable (as opposed to a stabilization provided by a handgrip).

Accordingly, there exists a need for an improved objective muscle strength testing method and device that uses the comfort and the grip of the naked hand of the examiner as the only direct support assistance and/or resistance.

OBJECTS OF THE INVENTION

It is therefore a general object of the present invention to provide a muscle strength testing method and apparatus that obviates the above-noted disadvantages.

An advantage of the present invention is that the muscle strength testing method and apparatus enables testing of most muscles and group of muscles of a human body.

A further advantage of the present invention is that the muscle strength testing method and apparatus provides sufficient sensitivity to objectively detect anything ranging from extremely small forces or muscle effort (even when the patient is unable to displace his/her body part against natural gravity) to normal large forces generated by limb muscles.

Yet another advantage of the present invention is that the muscle strength testing method and apparatus remains essentially manual in practice and enables simultaneous qualitative subjective and quantitative objective testing of muscles without interfering on or modifying the test itself.

Advantages of the present invention include the fact that the present muscle strength testing method and apparatus is specifically configured so as to be easy to use in a manner closely akin to the testing that examiners such as physicians, therapists, athletic trainers, coaches and the like currently use.

The muscle strength testing method and apparatus can be readily positioned so as to test various muscles or groups of muscles without the need for elaborate attachment to the patient and thus provides for a time efficient solution. Also, the present muscle strength testing method and apparatus affords accurate measurements and repeatability in its strength indication from one test to the next.

The present muscle strength testing method and apparatus by allowing use of a method closely akin to the currently highly performed manual method allows the examiner to obtain both a conventional subjective evaluation of the muscle strength and a more objective dynamometric numerical value of the patient's muscle strength. By allowing the hand of the examiner to provide for resistive forces during the strength evaluation process the muscle strength testing method and apparatus reduces set-up time consumption and sometimes complex set-up procedures.

Furthermore, the present muscle strength testing method and apparatus allows for the elimination of gravity induced biases and thus allows for the evaluation of even very weak muscles.

The present muscle strength testing method and apparatus provides various options such as the display of strength versus time curves, the recall of previous test values, the storage of various test values in electronic memory, the electronic linkage to various computing means for processing of the information.

Still further, the present muscle strength testing method and apparatus allows for measuring, recording and displaying of the strength of various muscles or groups of muscles and of strength peak values during effort.

Other objects and advantages of the present invention will become apparent from a careful reading of the detailed description provided herein, with appropriate reference to the accompanying drawings.

SUMMARY OF THE INVENTION

According to one aspect of the present invention, there is provided a muscle strength testing method for allowing an intended examiner to assess a muscular contraction of a selected muscle of a patient and the strength of the muscular contraction, the selected muscle being anatomically coupled to a target body part of the patients the patient further defining a patient non-target body part spaced from the patient target body part, the examiner having an examiner contacting body part for contacting the patient target body part and an examiner non-contacting body part spaced from the examiner contacting body part, the method allowing simultaneously the assessment of the muscular contraction of the selected muscle through direct contact between the examiner contacting body part and the patient target body part and the assessment of the strength of the muscular contraction of the selected muscle through the use of a pressure sensor, the method comprises the steps of positioning the pressure sensor so that the force exerted by the selected muscle during contraction thereof is transmitted indirectly to the pressure sensor without direct contact between the pressure sensor and the patient target body part; allowing the selected muscle to contract; allowing the examiner to assess by direct contact between the patient target body part and the examiner contacting body part the muscular contraction of the selected muscle and the strength of the muscular contraction; and providing a force value for the strength of said muscular contraction of the selected muscle through the use of the pressure sensor.

In one embodiment, the pressure sensor is positioned so as to be in contact with the examiner non-contacting body part, the force exerted by the selected muscle during contraction thereof being transmitted to the pressure sensor from the selected muscle to the patient target body part, from the patient target body part to the examiner contacting body part, from the examiner contacting body part to the examiner non-contacting body part and from the examiner non-contacting body part to the pressure sensor.

Typically, the method further comprises the step of: positioning a supporting component intermediate the examiner non-contacting body part and the pressure sensor so that the force exerted by the selected muscle during contraction thereof is transmitted from the examiner non-contacting body part to the supporting component and from the supporting component to the pressure sensor.

In one embodiment, the pressure sensor is positioned so as to be in contact with the patient non-target body part, the force exerted by the selected muscle during contraction thereof being transmitted to the patient target body part and from the patient target body part to the examiner contacting body part, the examiner contacting body part exerting an opposite reaction force on the patient target body part, the reaction force being generally equal to the selected muscle force, the reaction force being transmitted to the pressure sensor, from the patient target body part to the patient non-target body part, and from the patient non-target body part to the pressure sensor.

Typically, the method further comprises the step of: positioning a supporting component intermediate the patient non-target body part and the pressure sensor so that the reaction force exerted by the examiner contacting body part is transmitted from the patient non-target body part to the supporting component and from the supporting component to the pressure sensor.

Typically, the supporting component defines a body interfacing section and a sensor interfacing section, the body interfacing section supporting the patient non-target body part, and the sensor interfacing section contacting the pressure sensor.

In one embodiment, the sensor interfacing section includes at least two legs, and the pressure sensor includes at least two sensor devices, each of the sensor devices supporting a respective one of the legs, the force value corresponding to the strength of the selected muscle being provided through the use of the at least two sensor devices.

In one embodiment, the force value is evaluated by subtracting a first force value from a second force value transmitted indirectly to the pressure sensor, the first and second force values resulting from the contraction of the selected muscle while the selected muscle is respectively in a first and a second contracting state, the examiner contacting body part directly contacting the patient target body part during at least one of the first and second contracting states of the selected muscle.

Typically, the first contracting state is a relaxed state of the selected muscle, the first force value including a weight of at least a portion of said patient target body part; the examiner contacting body part applying an opposition to the force exerted by the selected muscle during muscular contraction thereof in the second contracting state on the patient target body part so as to substantially reduce movement of the patient target body part, the second force value including the weight of the at least a portion of the patient target body part; the step of providing a force value on the strength of the selected muscle through the use of the pressure sensor including: subtracting the first force value from the second force value so as to evaluate the force value for the strength of said muscular contraction of the selected muscle through the use of the pressure sensor, thereby canceling off the weight of the at least a portion of the patient target body part included in both the first and second force values.

In one embodiment, the method further includes the step of: positioning the patient target body part in a substantially horizontal orientation so that the force exerted by the selected muscle during contraction thereof is in a substantially vertical orientation.

In one embodiment, the pressure sensor is connectable to a computer member, the computer member including a display member connected thereto and a database, the database containing set-up data related to a plurality of muscles of the patient, the selected muscle being selectable from the plurality of muscles, the set-up data including information on positioning of the patient target body part, patient non-target body part, examiner contacting body part, examiner non-contacting body part and pressure sensor relative to each other for each one of the plurality of muscles, the method further includes the steps of: selecting the selected muscle from the plurality of muscles of the database of the computer member; displaying the set-up data information corresponding to the selected muscle on the display member; and displaying the force value for the strength of said muscular contraction of the selected muscle on the display member.

According to another aspect of the present invention, there is provided a muscle strength testing apparatus for allowing an intended examiner to assess a muscular contraction of a selected muscle of a patient and the strength of the muscular contraction, the selected muscle being anatomically coupled to a target body part of the patient, the patient further defining a patient non-target body part spaced from the patient target body part, the examiner having an examiner contacting body part for contacting the patient target body part and an examiner non-contacting body part spaced from the examiner contacting body part, the apparatus allowing the assessment of the muscular contraction of the selected muscle and the strength of the muscular contraction by the examiner through direct contact between the examiner contacting body part and the patient target body part, the apparatus comprises: a pressure sensor for sensing the strength of the muscular contraction of the selected muscle; a means for positioning the pressure sensor so that the force exerted by the selected muscle during contraction thereof is transmitted indirectly to the pressure sensor without direct contact between the pressure sensor and the patient target body part while allowing direct contact between the examiner contacting body part and the patient target body part; and a controller device connecting to the pressure sensor for providing information on the strength of the selected muscle through the use of the pressure sensor, the controller device assessing a force value transmitted to the pressure sensor and corresponding to the force exerted by the selected muscle.

Typically, the controller device includes an operator interface and a display member, the operator interface allowing an operator to activate the controller device, and the display member displaying the force value sensed by the pressure sensor.

In one embodiment, the pressure sensor includes at least two sensor devices, the force exerted by the selected muscle being transmitted to the at least two sensor devices, each of the sensor devices connecting to the controller device so that the controller device assesses the force value transmitted to the at least two sensor devices and resulting from the force exerted by the contraction of the selected muscle while the selected muscle.

In one embodiment, the force value is evaluated by subtracting a first force value from a second force value transmitted indirectly to the pressure sensor, the first and second force values resulting from the contraction of the selected muscle while the selected muscle is respectively in a first and a second contracting state, the controller device assessing the force value from the first and second force values transmitted to the pressure sensor and corresponding to the force exerted by the selected muscle while the selected muscle is respectively in the first and second contracting states.

Typically, the controller device includes an electronic circuit and a display member, the electronic circuit connecting to the pressure sensor for assessment of the first and second force values, the display member connecting to the electronic circuit to display the force value corresponding to the force exerted by the selected muscle and evaluated from the first and second force values.

In one embodiment, the electronic circuit assesses the first force value by averaging at least two first force value readings, the first force value readings being sensed by the pressure sensor over a pre-determined first time period during which the selected muscle is in the first contracting state. The second force value is a profiled force value occurring over a pre-determined second time period, the profiled second force value including at least two second force value readings, the electronic circuit assessing the second force value by subtracting the averaged first force value from each one of the second force value readings so as to provide a profiled force value for the strength of said muscular contraction of the selected muscle during contraction thereof.

Typically, the electronic circuit includes a storage memory, the storage memory storing the first and second force values.

In one embodiment, the controller device further includes a computer member connectable to the electronic circuit, the computer member including a database, the database containing set-up data related to a plurality of muscles of the patient, the selected muscle being selectable from the plurality of muscles, the set-up data including information on positioning of the patient target body part, patient non-target body part, examiner contacting body part, examiner non-contacting body part and pressure sensor relative to each other for each one of the plurality of muscles, the set-up data information being displayable on the display member.

In one embodiment, the controller device includes a remote activating switch connected thereto for remotely activating the controller device.

In one embodiment, the apparatus is portable.

In one embodiment, the means includes a supporting component adapted to be positioned intermediate the examiner non-contacting body part and the pressure sensor so that the force exerted by the selected muscle during contraction thereof is transmitted to the pressure sensor from the selected muscle to the patient target body part, from the patient target body part to the examiner contacting body part, from the examiner contacting body part to the examiner non-contacting body part, from the examiner non-contacting body part to the supporting component and from the supporting component to the pressure sensor.

In one embodiment, the means includes a supporting component adapted to be positioned intermediate the patient non-target body part and the pressure sensor so that the force exerted by the selected muscle during contraction thereof is transmitted to the pressure sensor from the selected muscle to the patient target body part, from the patient target body part to the examiner contacting body part, the examiner contacting body part exerting an opposite reaction force on the patient target body part, the reaction force being generally equal to the selected muscle force, the reaction force being transmitted to the pressure sensor, from the patient target body part to the patient non-target body part, from the patient non-target body part to the supporting component, and from the supporting component to the pressure sensor.

BRIEF DESCRIPTION OF THE DRAWINGS

In the annexed drawings, like reference characters indicate like elements throughout.

DETAILED DESCRIPTION OF THE PREFERRED EMBODIMENTS

With reference to the annexed drawings the preferred embodiments of the present invention will be herein described for indicative purpose and by no means as of limitation.

Figure 1:
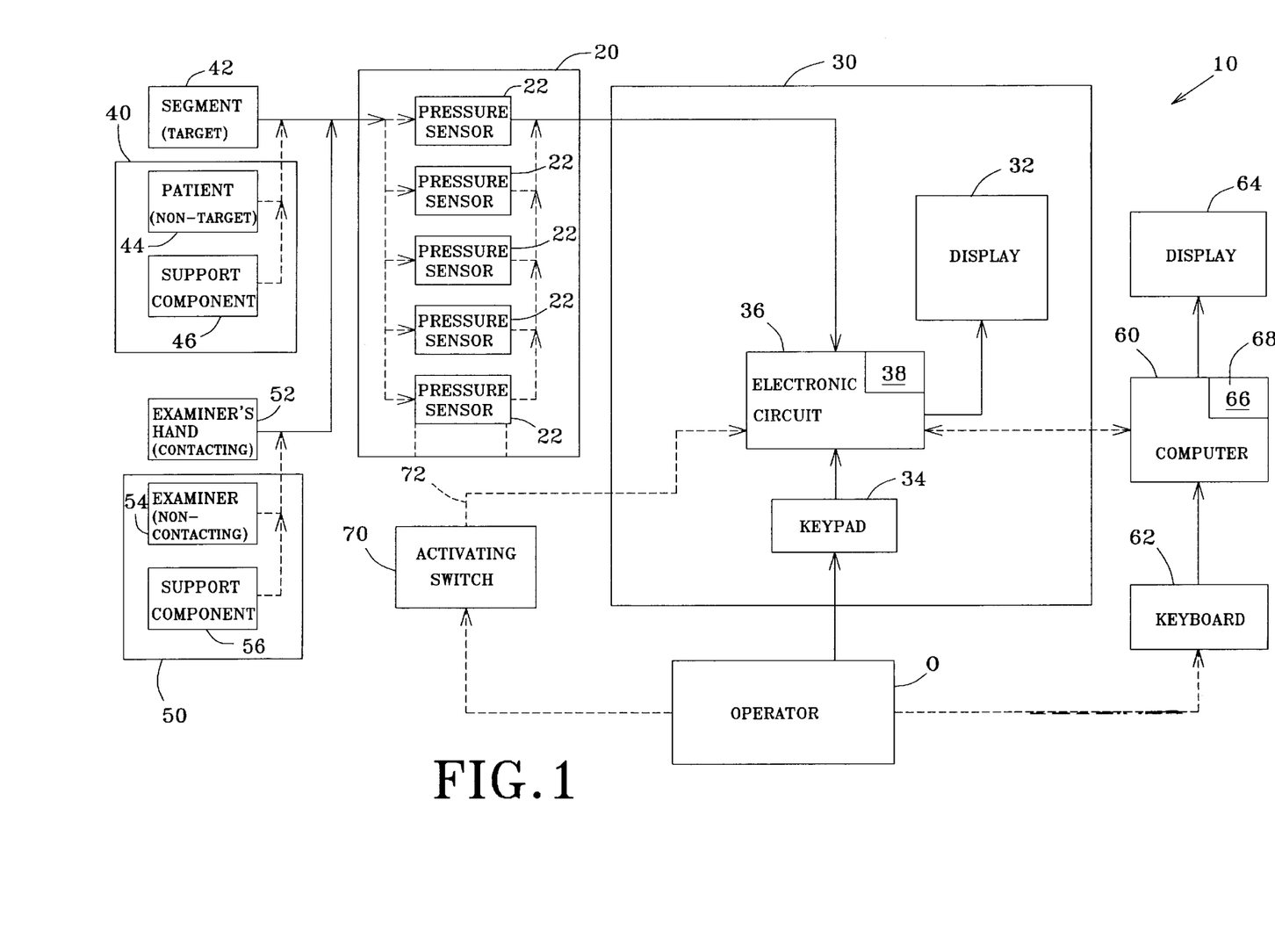
FIG. 1 is a schematic diagram of an embodiment of a muscle strength testing apparatus according to the present invention, illustrating the interactions between the different components of the apparatus, the dashed lines indicating interactions with optional components.

Referring to FIG. 1, there is shown an embodiment 10 of a muscle strength testing apparatus according to the present invention. The apparatus 10 includes a force responsive sensor device 20, preferably at least one pressure sensor member 22, such as load cell type force sensor or the like, adapted to be strategically positioned at various location(s) as will be hereinafter disclosed. The apparatus 10 also includes a controller device 30 connected to the sensor device 20 for electrically measuring forces applied to the pressure sensors 22. The controller device 30 typically has a display member 32 for displaying any output information from the controller 30 and a keypad member 34 for activating/starting the controller 30 by an operator O entering input information.

Figure 2:
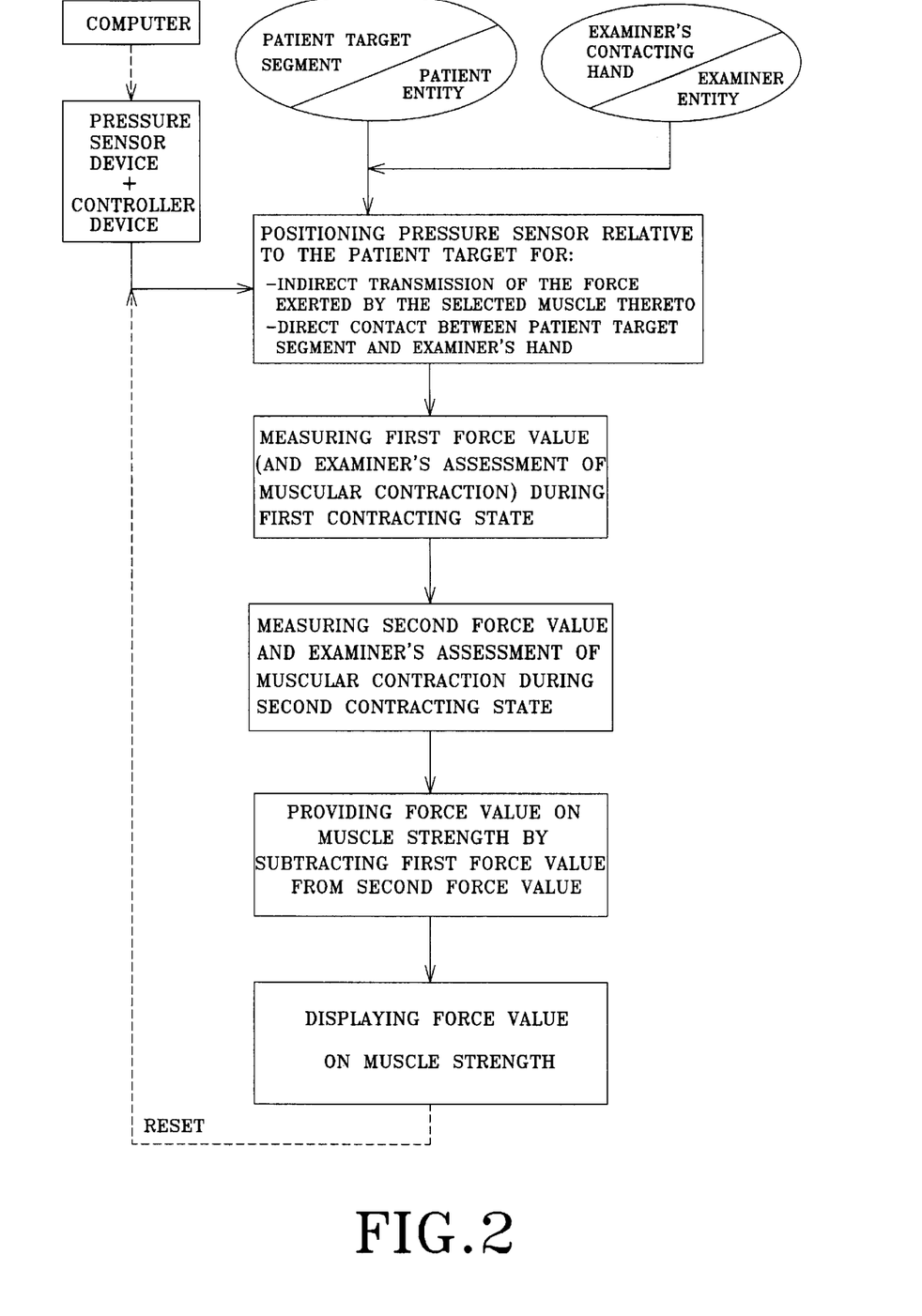
FIG. 2 is a flow diagram of an embodiment of a muscle strength testing method according to the present invention, showing the sequential steps of the method.

As illustrated in FIG. 2, the present invention also relates to a corresponding method of testing and measuring muscle strength. This method is typically based on the premise that once gravitational forces have been taken into account, any modification to the vertical force value exerted on the force responsive sensor device 20 under muscular contraction of the patient's selected muscle will provide an accurate read out of the muscle strength of such muscle. Although the present description refers to the selected muscle of a patient, it should be understood that it similarly refers to a selected group of muscles without departing from the scope of the present invention. Accordingly, it is well known in the art that it could rather be impossible for a patient to contract a specific muscle as opposed to a group of muscles including that specific muscle depending on the test configuration.

The method allows an intended examiner to assess the muscular contraction of the selected muscle of the patient and the strength of the muscular. contraction while a pressure sensor device 20 assesses the strength of the. muscular contraction. The selected muscle is anatomically coupled to a target body part or segment 42 of the patient such that its contraction induces a "virtual" displacement of the segment 42, since no real displacement occurs as explained hereinbelow. The patient generally includes a non-target body part 44 spaced from the target body part 42. Similarly, the examiner generally includes an examiner contacting body part 52, generally his/her naked or bare hand(s), for contacting the patient target body part 42 and an examiner non-contacting body part 54 spaced from the examiner contacting body part 52.

Figure 4:
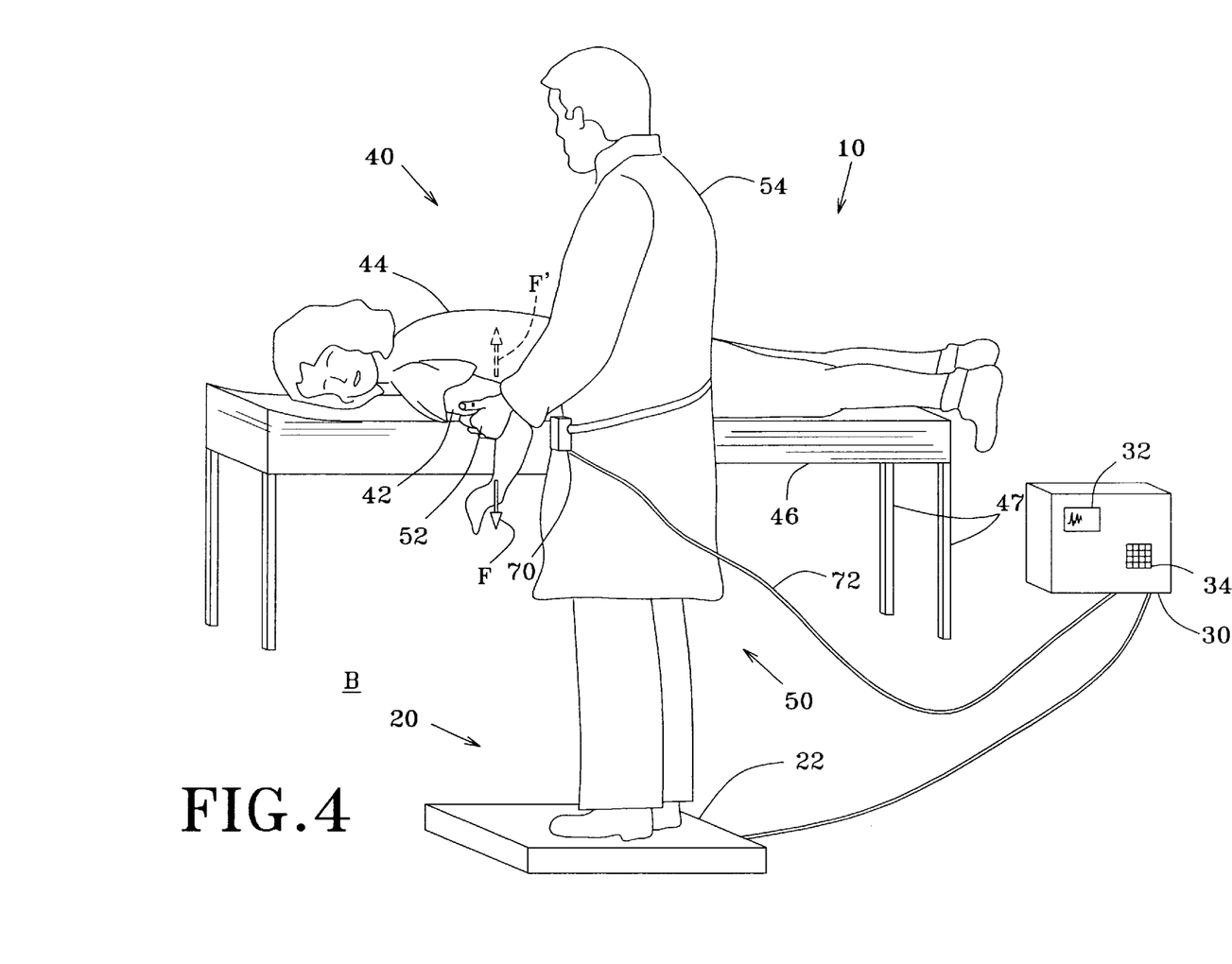
FIG. 4 is a schematic perspective view similar to FIG. 3, showing the apparatus being used for measuring the strength of the muscular contraction of a selected muscle of a patient, the patient resting on a table and vertically pushing his arm down or lifting it up against the opposition of an examiner standing nearby on a pressure sensor.

More specifically, the method allows both the assessment of the muscular contraction of the selected muscle through direct contact between the examiner's hand 52 and the patient segment 42 (no pressure sensor or the like in-between the two), and the simultaneous assessment of the strength of the muscular contraction of the selected muscle through the use of the pressure sensor device 20. Accordingly, the pressure sensor device 20 is positioned so that the force exerted by the selected muscle during contraction thereof is transmitted indirectly to the sensor device 20 without direct contact between the latter and the patient segment 42. In one embodiment, the force is transmitted to the sensor device 20 from the selected muscle to the patient segment 42, then to the examiner contacting body part 52, and then to the sensor device 20 through an examiner entity 50 including the examiner non-contacting body part 54, as illustrated in FIG. 4.

Figure 5:
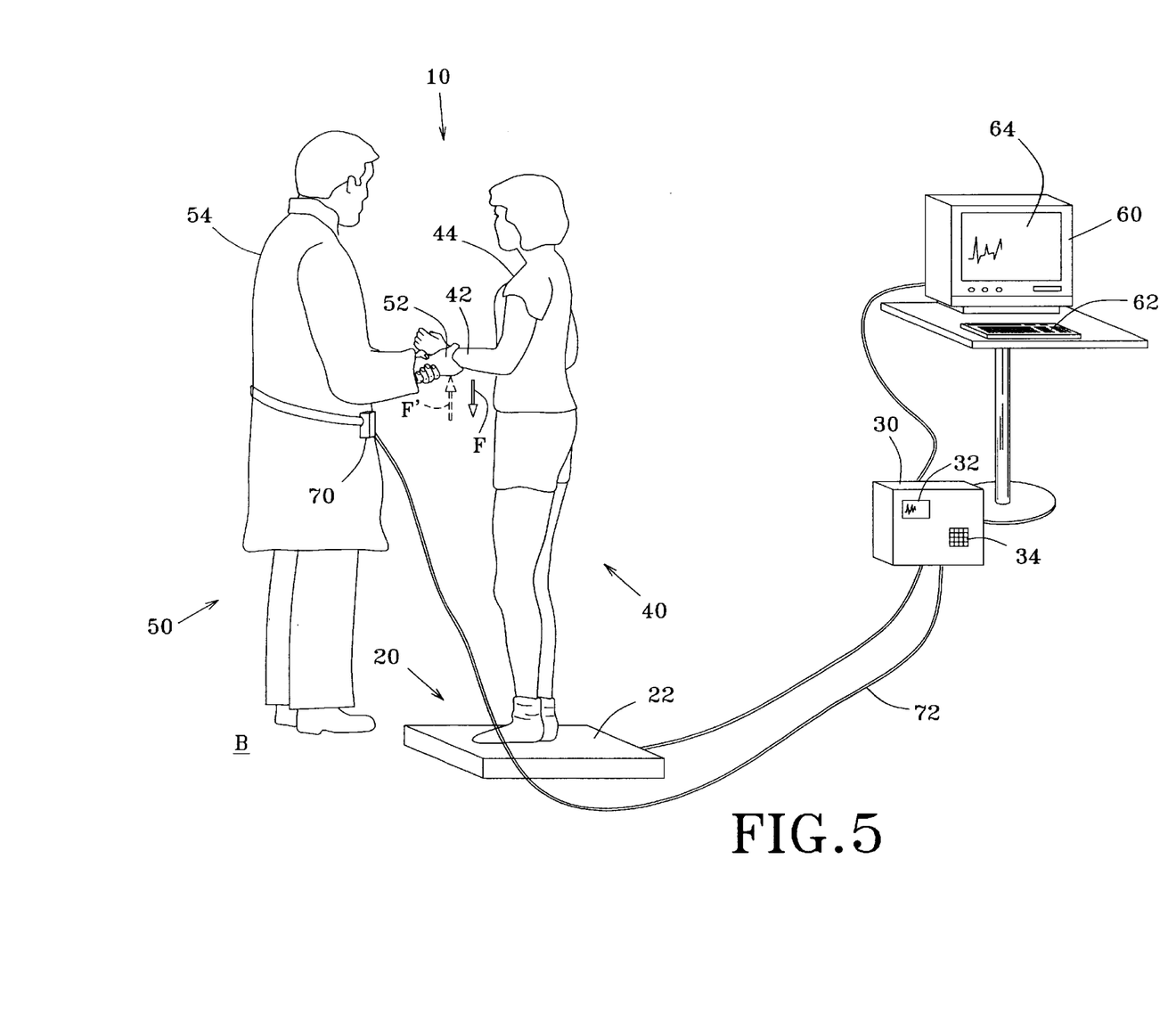
FIG. 5 is a schematic perspective view, showing the apparatus being used for measuring the strength of the muscular contraction of a selected muscle of a patient, the patient standing up on a pressure sensor and vertically pushing his arm down or lifting it up (as shown in dashed lines) against the opposition of an examiner standing nearby.

Similarly in another embodiment, the force is transmitted to the sensor device 20 from the selected muscle to the patient segment 42, then to the examiner contacting body part 52. The latter exerts an opposite reaction force, substantially equal to the muscle force F, transmitted back to the patient segment 42, and then to the sensor device through a patient entity 40 including the patient non-target body part 44, as illustrated in FIG. 5.

Typically, the method requires a proper positioning of the patient segment 42 related to the selected muscle(s) of which the force is being evaluated in a generally horizontal relationship relative to the line of gravity in such a manner as to allow the selected muscle(s) of the patient to exert a force F in a generally vertical orientation on the segment 42. A first force (reference, or tare) value is established by measuring a weight applied to strategically installed or positioned pressure sensors 22 when the muscle is in a first contracting state, typically a relaxed state (at rest) or any other non-relaxed state required to maintain a pre-determined position of the segment 42, for example against gravity as explained hereinbelow. This step allows correction for the gravitational weight of the segment 42 being evaluated either in the positive or negative direction depending on the vertical direction of the movement relative to the gravitational force, by eliminating its effect, including the effect of the weight of any other component such as the patient entity 40 or the examiner entity 50 that is sensed the pressure sensors 22. It provides the controller device 30 and the examiner with a read out not only of the force exerted by the selected muscle, but also of the force required by the muscle to maintain the segment 42 against gravity, which will be subtracted later on. Once the reference value has been established the patient is typically asked to exert a maximum force F, corresponding to a second contracting state of the selected muscle, in the vertical direction against an opposition or resistance provided by the examiner, resulting in a pressure on the segment 42. Depending on the muscle testing configuration, the examiner contacting body part 52 contacts the patient target body part 42 during either one of the first and second contracting states of the selected muscle or during both, as required.

Modulations of the read outs by the pressure sensors 22 being strategically positioned provides for a generally accurate read out information on the strength of the selected muscle(s).

More specifically, the method consists in
  positioning the pressure sensor 22 so that the force exerted by the selected muscle during contraction thereof is transmitted indirectly to the pressure sensor 22 without direct contact between the pressure sensor 22 and the patient target body part 42;
  allowing the selected muscle to contract;
  allowing the examiner 54 to assess by direct contact between the patient target body part 42 and the examiner contacting body part 52 the muscular contraction of the selected muscle and the strength of the muscular contraction; and
  providing a force value for the strength of the muscular contraction of the selected muscle through the use of the pressure sensor 22.

Therefore, a resistance offered by the examiner provides for a qualitative and subjective evaluation as obtained through the conventional manual muscle strength testing method. The pressure sensors 22 could then be strategically positioned directly in contact with either the patient non-target body part 44 or the examiner non-contacting body part 54, as shown in FIGS. 5 and 4, respectively.

Figure 3:
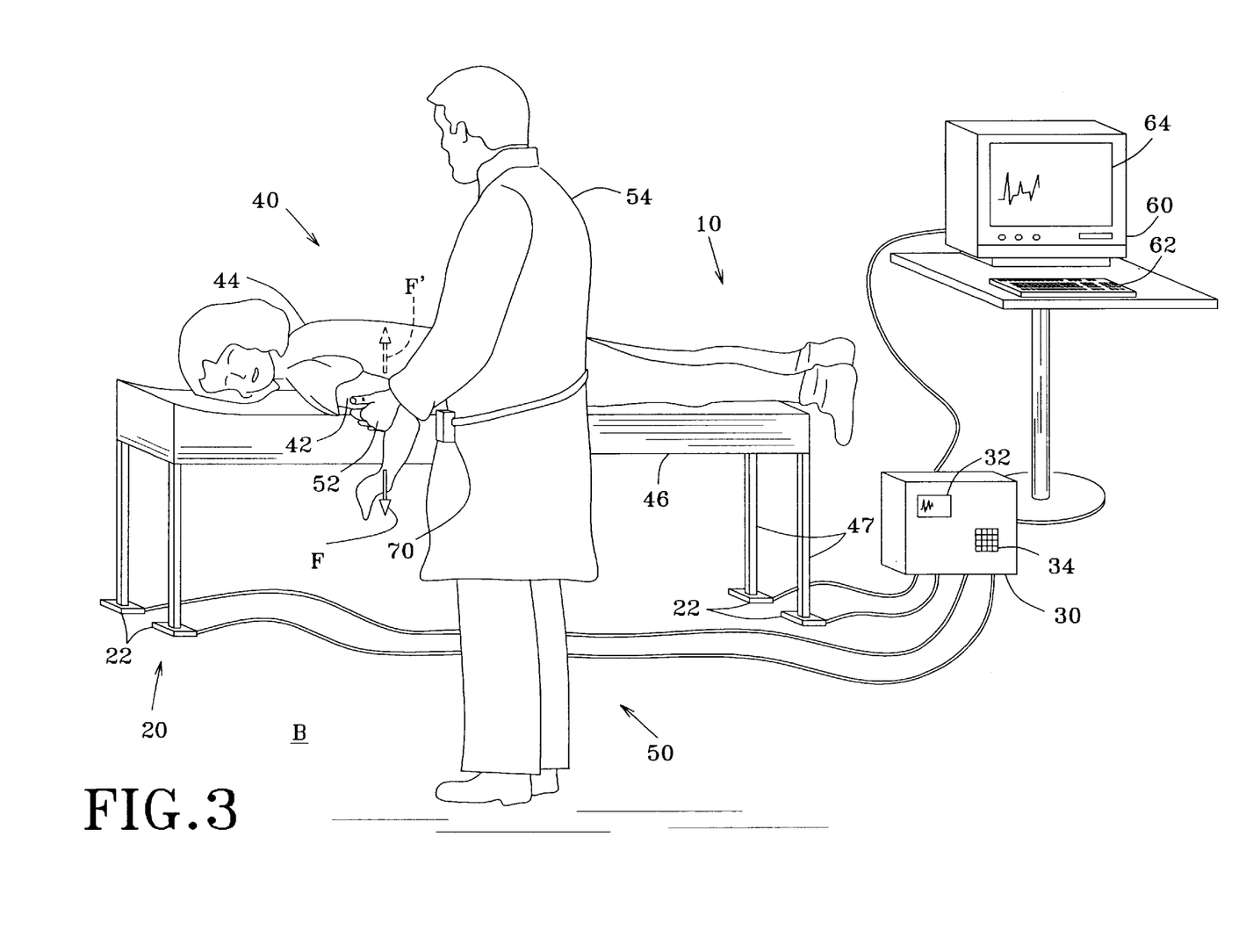
FIG. 3 is a schematic perspective view of the embodiment of FIG. 1, showing the apparatus being used for measuring the strength of the muscular contraction of a selected muscle of a patient, the patient resting on a table and pushing his/her arm down or lifting it up against the resistance of an examiner standing nearby, as shown in solid and dashed lines respectively, pressure sensors being positioned underneath the table legs.
Figure 6:
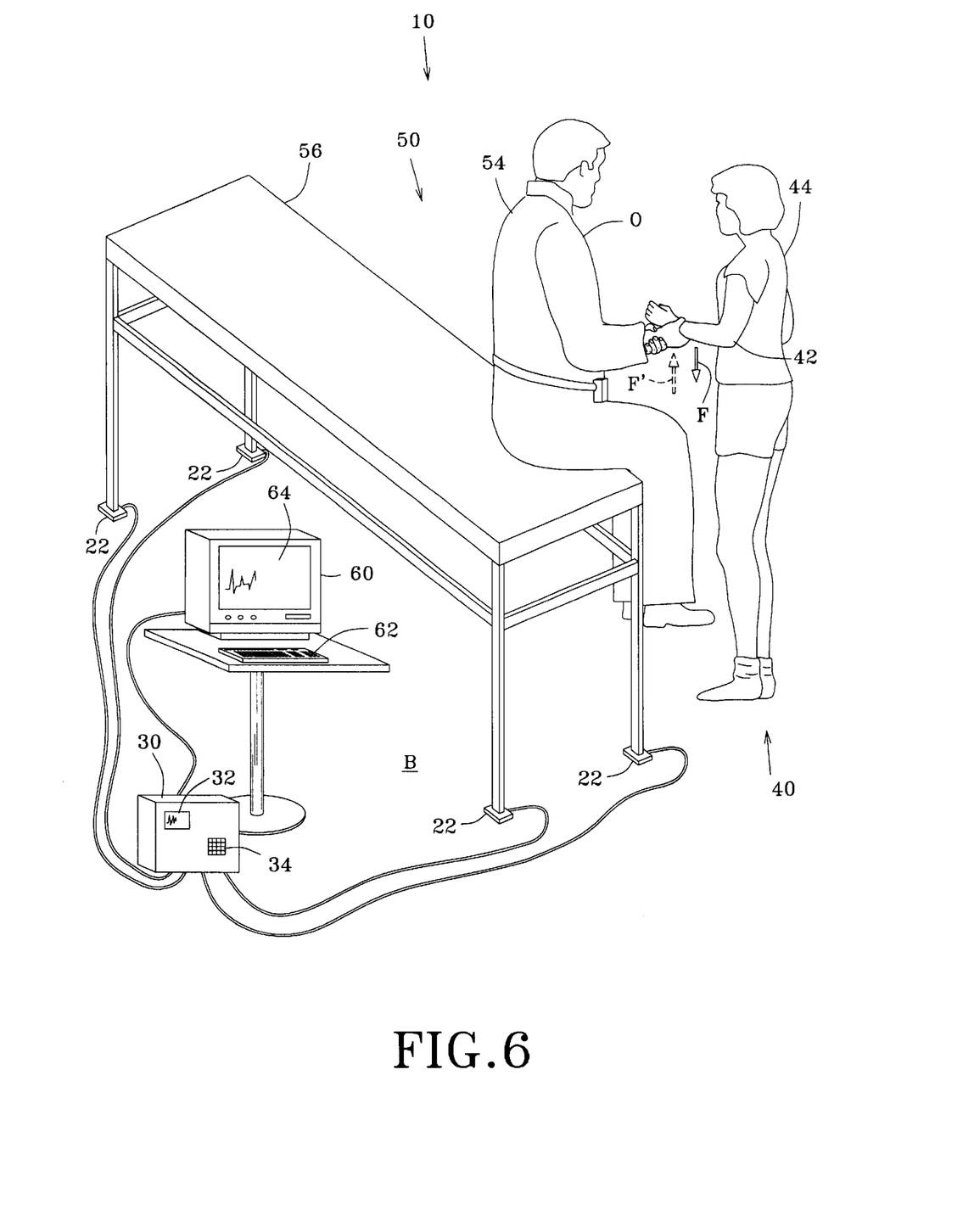
FIG. 6 is a schematic perspective view similar to FIG. 5, showing the apparatus being used for measuring the strength of the muscular contraction of a selected muscle of a patient, the patient standing up and vertically pushing his arm down or lifting it up (as shown in dashed lines) against the opposition of an examiner sitting nearby on a pressure sensor.

The method, in many configurations, further includes the step of positioning a supporting component or structure 56, 46 intermediate either the examiner non-contacting body part 54 or the patient non-target body part 44 and the pressure sensor 22, so that the force F exerted by the selected muscle during contraction thereof, or its equivalent reaction force, is transmitted from either the examiner non-contacting body part 54 or the patient non-target body part 44 to the supporting component 56, 46 and from the supporting component 56, 46 to the pressure sensor 22, as illustrated in FIG. 6 and FIG. 3 respectively. The supporting component 56, 46 is then assumed to be part of either the examiner entity 50 or the patient entity 40.

The supporting component 46, 56 generally defines a body interfacing section, such as the top planar surface of a table or the like, to support the patient non-target body part 44, and a sensor interfacing section, such as the legs 47 of the table or the like, that is in contact with the pressure sensor(s) 22.

Figure 3A:
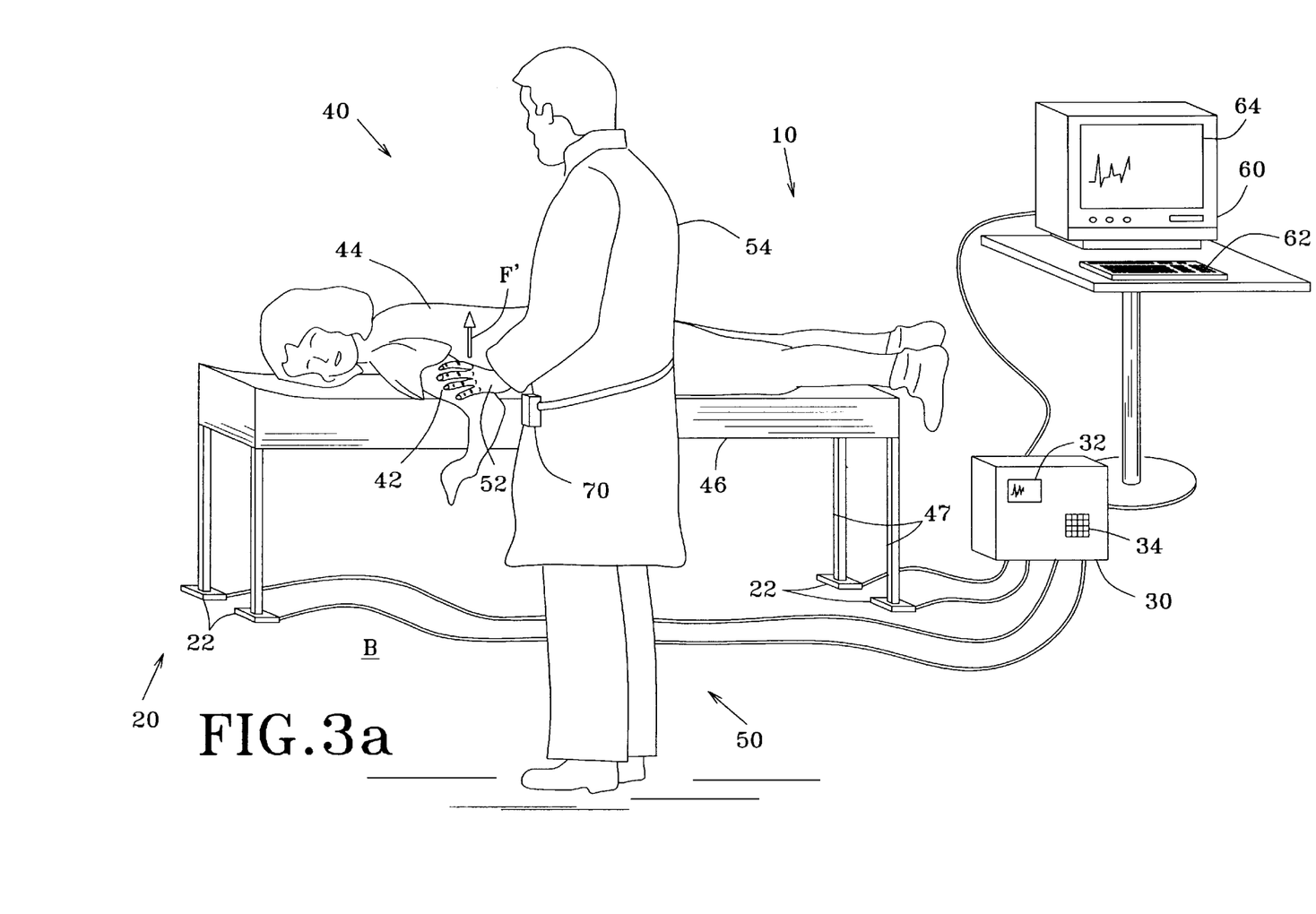
FIG. 3a is a view similar to FIG. 3, showing the apparatus being used for measuring the strength of the muscular contraction of a selected muscle of a patient, the patient resting on a table and vertically lifting his/her arm up against the resistance of the examiner standing nearby, as shown by the arrow; in this case, the examiner of illustration of FIG. 3 had previously supported the arm in a relaxed state to obtain the reference value that takes the gravity into account.

For example, in a situation such as the one schematically illustrated in FIGS. 3 and 3a, the patient entity 40, preferably the patient non-target body part 44 resting on its patient structure 46, such as a treatment table or the like, is intermediate between his/her segment 42, such as his/her arm, positioned substantially horizontally and the pressure sensors 22. The examiner entity 50, or examiner non-contacting body part 54, and the examiner contacting body part 52 are positioned so as to provide opposition to the downward force F, or upward force F', exerted by the selected muscle, specifically the shoulder flexors or extensors in this case respectively (FIGS. 3 and 3a), to measure the strength of the contraction thereof. Pressure sensors 22 may be positioned either underneath the table legs 47, or directly underneath the examiner non-contacting body part 54 as shown in FIG. 4. Once zeroing (measurement of first force or reference or neutral zero value) has occurred (as illustrated in FIG. 3), a second force value measurement is performed by the controller 30 when the selected muscle exerts a downward force F, or upward F', against the opposition of the examiner contacting body part 52 (as illustrated in FIGS. 3 and 3a), providing a relative accurate difference force value between the first and second force values, which is the strength of the patient's examined selected muscle(s), namely the shoulder flexors or extensors respectively.

In the above example, when the patient exerts a first effort to put the selected muscle(s) in a first contracting state, typically a relaxed state, for the measurement of the first force value, the examiner contacting body part 52 supports the segment 42 from underneath at a determined location associated with a specific lever arm (see FIG. 3). Then, upon the upwardly oriented force F' for the measurement of the second force value from the selected muscle of the patient, the examiner obviously needs to provide a resistance leverage at a similar location above the segment 42 via its contacting body part 52 (see FIG. 3a).

In situations illustrated in FIGS. 3 and 4, the examiner supporting the segment 42 under test has the privilege of performing a standard qualitative subjective evaluation of the muscular contraction simultaneously with the quantitative objective testing using the sensor device 20 as described hereinabove.

Similarly, the examiner supporting the segment 42 of the patient could be sitting on the table that would become the examiner structure 56, with the patient standing on the floor B as shown in FIG. 6, or being on another treatment table (not shown) or simply a chair or the like.

In an embodiment of the invention the pressure sensors 22 take the form of modified electronic weighing machines such as those used for weighing parcels, or load cells used in industrial applications, since they provide a high measurement accuracy of less than 40 grams (that could detect contraction of small muscles such as finger muscles and the like) and a wide measurement range from zero to over three hundred (300) kilograms. The fact that a difference value is calculated improves the accuracy of the apparatus, as opposed to an absolute value. As it would be obvious to anyone skilled in the art, pressure sensors 22 along with their respective connection to the controller device 30 are specifically adapted to exclude parasites.

As shown in FIG. 1, the controller 30 includes an electronic circuit member 36 connected to the pressure sensors 22 and the keypad member 34 to receive input information from the operator O. The electronic circuit 36 is further connected to the display member 32 as an output channel. The electronic circuit 36 also includes a storage memory 38 to store the different output information for further downloading and post-processing, as hereinafter described. Obviously, the controller 30 also includes all required interfaces for all connections, as it is well known in the art.

Typically, the controller 30 is so configured as to preferably read five (5) pressure sensors 22 although other configurations may be provided without departing from the scope of the present invention. Readings are performed quasi simultaneously in order to provide for better accuracy, with typically less than a few milliseconds as well known in the art. Typically, first and second force values are preferably force profile over time. Accordingly, the pressure sensors 22 are typically read at a rate of approximately one hundred (100) cycles per second per channel. The input rate could be higher up to one thousand (1000) cycles per second or more (or less) without departing from the scope of the present invention. The display member 32 typically takes the form of a liquid crystal type LCD display. Preferably, the display 32 provides information on the actual output information showing the peak strength value, prior test output values or any other suitable information. As is well known in the art, angulation and intensity of the LCD display may be adjusted through suitable adjustment means, if required.

A power source is further provided for powering various parts, components of the apparatus 10, as well known in the art. Typically, the power source includes re-chargeable batteries so as to provide for autonomy of the apparatus 10.

Accordingly, the apparatus 10 is adapted for being hand-carried by the examiner or operator O in order to be conveniently displaced to a patient's residence by the examiner or operator O visiting the handicapped or under rehabilitation patient. Therefore all test results are preferably stored in the apparatus memory 38 for further analysis by the examiner at his/her office.

When a connection is not being used on the controller 30, the signal for the specific input is adequately being treated as to eliminate interferences. Within the keypad 34, an activating switch is provided for initiating the test procedure. Optionally, the activating switch 70 may be actuated by the foot, the hands or any other suitable body part of the examiner or operator O if remotely connected using a connecting wire 72 or simply be wireless as often used in similar applications. Typically, the activating switch 70 is provided with a magnet so as to allow for the latter to be magnetically anchored to most metallic equipment.

Additionally, a pair of selecting switches are provided for allowing selective display and browsing of prior test output results. A reset switch is also preferably provided for resetting the apparatus 10. Audio display means may also optionally be provided to provide audio cues for enabling the examiner to follow step procedures in synchronization with the controller 30.

The electronic circuit 36 typically computes the output information emanating from the pressure sensors 22 through the controller 30 and preferably coordinates the different sequences of testing operation.

Once the apparatus 10 is activated, the electronic circuit 36 preferably initializes the input data, the LCD display 32, and all interfaces. The apparatus 10 then waits in a stand-by mode. Once the operator O or the examiner activates the activating switch 70 for a given test, the circuit 36 initiates the reading/recording process. Each reading sequence preferably includes a waiting time interval typically in the range of two (2) seconds prior to reading the reference (or first force) value on each pressure sensor 22. In order to read a reference value the circuit 36 communicates with pressure sensors 22 which transmit the respective weight or force data. The circuit 36 reads approximately one hundred (100) reading cycles on each channel. For better accuracy, an average first force value is computed every ten first force value readings in order to preserve approximately ten (10) readings per second, typical pre-determined first period, with the selected muscle in its first contracting state.

Once the reference value has been computed, the circuit 36 preferably waits for an additional waiting period substantially in the range of two (2) cycles prior to performing the strength measurement or second force value readings over a typical pre-determined second period duration of less than thirty (30) seconds (longer periods could be considered for performing endurance tests of the muscle(s), or the like tests) with the selected muscle in its second contracting state, which could obviously provide for a profiled force. The patient is instructed to activate the selected muscle in its second contracting state so as to create a vertical force F at segment 42, either downwardly or upwardly oriented. The circuit 36 subtracts the respective reference value to each second force value reading, on all pressure sensors 22, in order to obtain the difference value or the profiled force F exerted by the selected muscle of the patient. The difference force value is preferably computed immediately after each reading in order to enable real time output appearance on the display 32.

Figure 7:
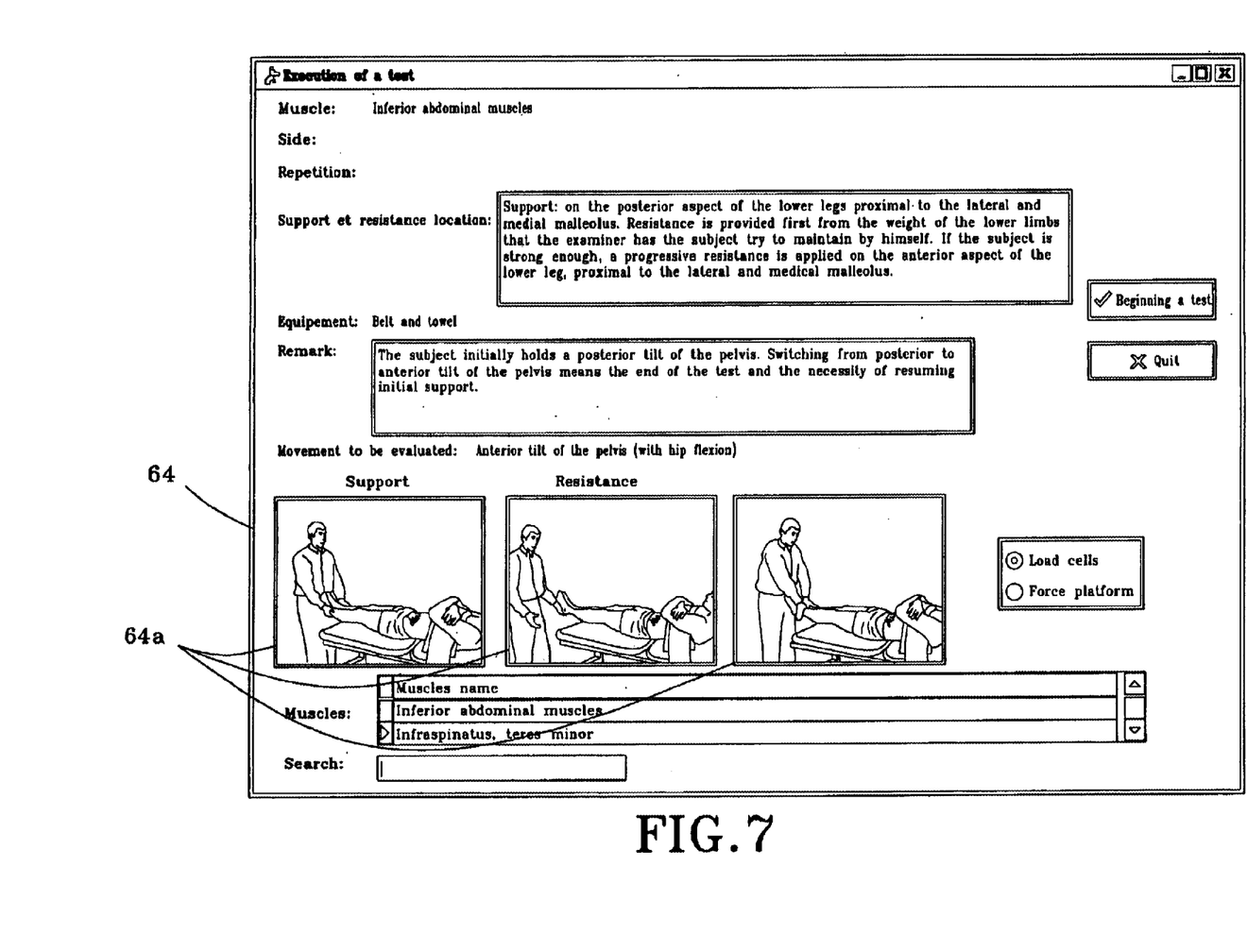
FIG. 7 is a diagram showing an example of a display of the computer showing illustrative pictorials of different selectable positions from a database to perform specific tests.

Once the test is finished for a given selected muscle strength, the electronic circuit 36 computes the peak force on a predetermined peak force range typically in the range of half a second (0.5 s) and displays the latter on the LCD display 32. All of the readouts and computed values are then stored in the storage memory 38. The apparatus 10 then returns to the stand-by mode. The circuit 36 of the controller 30 is also optionally connected to a computer member 60 to send all of the read, computed and stored values towards the same via a serial type interface so as to allow for proper transfer (or download). The computer 60, preferably a PC (or Macintosh®) type computer with its own keyboard 62 for operator input may optionally initiate any step sequence, display the input and output computed values on its own display screen 64 and store the computed and input values within its own memory 66. A calibration ratio may also be transferred to the computer in order to allow the latter to perform its own computing sequence. The electronic circuit 36 and preferably the computer 60 may be used for further data post-processing such as mathematical statistics or pre-processing such as other modular treatment to the input values and to manipulate the latter so as to facilitate cognitive sequential treatment. Essentially, the computer 60 determines the proper sequence of performing a series of tests to minimize displacement efforts to the patient as well as testing time. The computer 60 preferably includes a database 68, in its memory 66, providing, for each of the different possible selected muscle to be tested (over one hundred (100) and even more), information with description of the test set-up positions of the required examiner 50 and patient 40 entities (presence or not of any specific respective structure 56, 46), as well as corresponding examiner contacting body part 52 and patient target body part 42 test set-up positions, corresponding location of the pressure sensor(s) 22, and, preferably, corresponding illustrative pictorials 64a, as shown in FIG. 7 in which all the test set-up data information is generally displayed on the computer display screen 64. Also, the controller 30 provides capability for the operator O to calibrate the pressure sensors 22 whenever required through a programmed calibration procedure.

Optionally, in the case the location of the apparatus 10 remains permanent into a specific room, one could consider having the floor B of the room being subdivided in specific sections mounted on respective pressure sensors 22. The latter would thereby be embedded therein and seem invisible to the examiner and the patient while still being connected to the apparatus 10.

Although the present muscle strength testing method and apparatus have been described with a certain degree of particularity it is to be understood that the disclosure has been made by way of example only and that the present invention is not limited to the features of the embodiments described and illustrated herein, but includes all variations and modifications within the scope and spirit of the invention as hereinafter claimed.

We claim:

1. A muscle strength testing apparatus for allowing an intended examiner to assess a muscular contraction of a selected muscle of a patient and the strength of said muscular contraction, the selected muscle being anatomically coupled to a target body part of said patient, said patient further defining a patient non-target body part spaced from said patient target body part, said examiner having an examiner contacting body part for contacting said patient target body part and an examiner non-contacting body part spaced from said examiner contacting body part, said apparatus allowing the assessment of said muscular contraction of the selected muscle and the strength of said muscular contraction by said examiner through direct contact between said examiner contacting body part and said patient target body part, said apparatus comprising;

a pressure sensor for sensing the strength of said muscular contraction of the selected muscle;

means for positioning said pressure sensor so that the force exerted by the selected muscle during contraction thereof is transmitted indirectly to said pressure sensor without direct contact between said pressure sensor and said patient target body part while allowing direct contact between said examiner contacting body part and said patient target body part; and a controller device connecting to said pressure sensor for providing information on the strength of the selected muscle through the use of said pressure sensor, said controller device assessing a force value transmitted to said pressure sensor and corresponding to said force exerted by the selected muscle.

2. The apparatus of claim 1 wherein said controller device includes an operator interface and a display member, said operator interface allowing an operator to activate said controller device, and said display member displaying said force value sensed by said pressure sensor.

3. The apparatus of claim 2 wherein said pressure sensor includes at least two sensor devices, said force exerted by the selected muscle being transmitted to said at least two sensor devices, each of said sensor devices connecting to said controller device so that said controller device assesses said force value transmitted to said at least two sensor devices and resulting from the force exerted by the contraction of the selected muscle.

4. The apparatus of claim 1 wherein said force value is evaluated by subtracting a first force value from a second force value transmitted indirectly to said pressure sensor, said first and second force values resulting from the contraction of the selected muscle while the selected muscle is respectively in a first and a second contracting state, said controller device assessing said force value from said first and second force values transmitted to said pressure sensor and corresponding to the force exerted by the selected muscle while the selected muscle is respectively in said first and second contracting states.

5. The apparatus of claim 4 wherein said controller device includes an electronic circuit and a display member, said electronic circuit connecting to said pressure sensor for assessment of said first and second force values, said display member connecting to said electronic circuit to display said force value corresponding to the force exerted by the selected muscle and evaluated from said first and second force values.

6. The apparatus of claim 5 wherein said electronic circuit assesses said first force value by averaging at least two first force value readings, said first force value readings being sensed by said pressure sensor over a pre-determined first time period during which the selected muscle is in said first contracting state.

7. The apparatus of claim 6 wherein said second force value is a profiled force value occurring over a pre-determined second time period, said profiled second force value including at least two second force value readings, said electronic circuit assessing said second force value by subtracting said averaged first force value from each one of said second force value readings so as to provide a profiled force value for the strength of said muscular contraction of the selected muscle during contraction thereof.

8. The apparatus of claim 5 wherein said electronic circuit includes a storage memory, said storage memory storing said first and second force values.

9. The apparatus of claim 5 wherein said controller device further includes a computer member connectable to said electronic circuit, said computer member including a database, said database containing set-up data related to a plurality of muscles of said patient, the selected muscle being selectable from said plurality of muscles, said set-up data including information on positioning of said patient target body part, patient non-target body part, examiner contacting body part, examiner non-contacting body part and pressure sensor relative to each other for each one of said plurality of muscles, the set-up data information being displayable on said display member.

10. The apparatus of claim 1 wherein said controller device includes a remote activating switch connected thereto for remotely activating said controller device.

11. The apparatus of claim 1 wherein said apparatus is portable.

12. The apparatus of claim 1 wherein said means includes a supporting component adapted to be positioned intermediate said examiner non-contacting body part and said pressure sensor.

13. The apparatus of claim 1, wherein said means includes a supporting component adapted to be positioned intermediate said patient non-target body part and said pressure sensor.

14. The apparatus of claim 13 wherein said supporting component defines a body interfacing section and a sensor interfacing section, said body interfacing section being adapted to support said patient non-target body part, and said sensor interfacing section contacting said pressure sensor.

15. The apparatus of claim 14 wherein said sensor interfacing section includes at least two legs, and wherein said sensor includes at least two sensor devices, each of said sensor devices supporting a respective one of said legs, each of said sensor devices connecting to said controller device, said controller device assessing said force value transmitted to said sensor devices and corresponding to the force exerted by the selected muscle.

16. A muscle strength testing method for allowing an intended examiner to assess a muscular contraction of a selected muscle of a patient and the strength of said muscular contraction, the selected muscle being anatomically coupled to a target body part of said patient, said patient further defining a patient non-target body part spaced from said patient target body part, said examiner having an examiner contacting body part for contacting said patient target body part and an examiner non-contacting body part spaced from said examiner contacting body part, said method allowing simultaneously the assessment of said muscular contraction of the selected muscle through direct contact between said examiner contacting body part and said patient target body part and the assessment of the strength of said muscular contraction of the selected muscle through the use of a pressure sensor, said method comprising the steps of:

positioning said pressure sensor so that the force exerted by the selected muscle during contraction thereof is transmitted indirectly to said pressure sensor without direct contact between said pressure sensor and said patient target body part;

allowing the selected muscle to contract;

allowing said examiner to assess by direct contact between said patient target body part and said examiner contacting body part said muscular contraction of the selected muscle and the strength of said muscular contraction;

providing a force value for the strength of said muscular contraction of the selected muscle through the use of said pressure sensor.

17. The method of claim 16 wherein said pressure sensor is positioned so as to be in contact with said examiner non-contacting body part, said force exerted by the selected muscle during contraction thereof being transmitted to said pressure sensor from the selected muscle to said patient target body part, from said patient target body part to said examiner contacting body part, from said examiner contacting body part to said examiner non-contacting body part and from said examiner non-contacting body part to said pressure sensor.

18. The method of claim 17, further comprising the step of:

positioning a supporting component intermediate said examiner non-contacting body part and said pressure sensor so that the force exerted by the selected muscle during contraction thereof is transmitted from said examiner non-contacting body part to said supporting component and from said supporting component to said pressure sensor.

19. The method of claim 16 wherein said pressure sensor is positioned so as to be in contact with said patient non-target body part, said force exerted by the selected muscle during contraction thereof being transmitted to said patient target body part and from said patient target body part to said examiner contacting body part, said examiner contacting body part exerting an opposite reaction force on said patient target body part, said reaction force being generally equal to said selected muscle force, said reaction force being transmitted to said pressure sensor, from said patient target body part to said patient non-target body part, and from said patient non-target body part to said pressure sensor.

20. The method of claim 19, further comprising the step of:

positioning a supporting component intermediate said patient non-target body part and said pressure sensor so that the reaction force exerted by said examiner contacting body part is transmitted from said patient non-target body part to said supporting component and from said supporting component to said pressure sensor.

21. The method of claim 20 wherein said supporting component defines a body interfacing section and a sensor interfacing section, said body interfacing section supporting said patient non-target body part, and said sensor interfacing section contacting said pressure sensor.

22. The method of claim 21 wherein said sensor interfacing section includes at least two legs, and wherein said pressure sensor includes at least two sensor devices, each of said sensor devices supporting a respective one of said legs, said force value corresponding to the strength of the selected muscle being provided through the use of said at least two sensor devices.

23. The method of claim 16 wherein said force value is evaluated by subtracting a first force value from a second force value transmitted indirectly to said pressure sensor, said first and second force values resulting from the contraction of the selected muscle while the selected muscle is respectively in a first and a second contracting state, said examiner contacting body part directly contacting said patient target body part during at least one of said first and second contracting states of the selected muscle.

24. The method of claim 23 wherein said first contracting state is a relaxed state of the selected muscle, said first force value including a weight of at least a portion of said patient target body part;

said examiner contacting body part applying an opposition to the force exerted by the selected muscle during muscular contraction thereof in said second contracting state on said patient target body part so as to substantially reduce movement of said, patient target body part, said second force value including said weight of said at least a portion of said patient target body part;

the step of providing a force value on the strength of the selected muscle through the use of said pressure sensor including:

subtracting said first force value from said second force value so as to evaluate said force value for the strength of said muscular contraction of the selected muscle through the use of said pressure sensor, thereby canceling off said weight of said at least a portion of said patient target body part included in both said first and second force values.

25. The method of claim 16, further including the step of:
   positioning said patient target body part in a substantially horizontal orientation so that the force exerted by the selected muscle during contraction thereof is in a substantially vertical orientation.

26. The method of claim 16 wherein said pressure sensor is connectable to a computer member, said computer member including a display member connected thereto and a database, said database containing set-up data related to a plurality of muscles of said patient, the selected muscle being selectable from said plurality of muscles, said set-up data including information on positioning of said patient target body part, patient non-target body part, examiner contacting body part, examiner non-contacting body part and pressure sensor relative to each other for each one of said plurality of muscles, said method further including the steps of:

selecting the selected muscle from said plurality of muscles of said database of said computer member;

displaying the set-up data information corresponding to the selected muscle on said display member;

displaying said force value for the strength of said muscular contraction of the selected muscle on said display member.

* * * * *